United States Patent [19]

Bashkansky et al.

[11] Patent Number: 5,303,710
[45] Date of Patent: Apr. 19, 1994

[54] APPARATUS FOR IMAGING AN OBJECT IN OR THROUGH A SCATTERING MEDIUM USING COHERENT ANTI-STOKES RAMAN SCATTERING

[75] Inventors: Mark Bashkansky; John F. Reintjes, both of Alexandria, Va.

[73] Assignee: The United States of America as represented by the Secretary of the Navy, Washington, D.C.

[21] Appl. No.: 970,886

[22] Filed: Nov. 3, 1992

[51] Int. Cl.$^5$ .............................................. A61B 6/00
[52] U.S. Cl. ................................. 128/665; 128/633; 128/664; 356/301
[58] Field of Search .................... 128/664, 665, 633; 356/301; 372/3

[56] References Cited

U.S. PATENT DOCUMENTS

| | | | |
|---|---|---|---|
| 4,178,079 | 12/1979 | Bjorklund et al. | 350/353 |
| 4,284,354 | 8/1981 | Liao | 356/301 |
| 4,488,308 | 12/1984 | McClain | 372/57 |
| 4,500,995 | 2/1985 | White | 372/3 |
| 4,555,176 | 11/1985 | Moore et al. | 356/301 |
| 4,648,714 | 3/1987 | Benner et al. | 128/665 |
| 4,750,153 | 6/1988 | Owechko et al. | 365/125 |
| 4,790,652 | 12/1988 | Unéus et al. | 356/45 |
| 4,796,992 | 1/1989 | Aoshima et al. | 356/347 |
| 4,832,483 | 5/1989 | Verma | 128/664 |
| 4,921,353 | 5/1990 | Chiou et al. | 356/347 |
| 4,945,239 | 7/1990 | Wist et al. | 250/358.1 |
| 4,948,212 | 8/1990 | Cheng et al. | 350/364 |
| 4,968,107 | 11/1990 | Yeh | 350/364 |
| 5,035,506 | 7/1991 | Ouhayoun | 356/349 |
| 5,095,487 | 3/1992 | Meyerhofer et al. | 372/23 |
| 5,140,463 | 8/1992 | Yoo et al. | 359/559 |
| 5,150,228 | 9/1992 | Liu et al. | 359/7 |

OTHER PUBLICATIONS

*Two-dimensional imaging through diffusing media using 150-fs gated electronic holography techniques*, H. Chen, Y. Chen, D. Dilworth, E. Leith, J. Lopez and J. Valdmanis, 1991 Optical Society of America, vol. 16, No. 7, Apr. 1, 1991, pp. 487–489.

Optical Society of American Annual Meeting, 1991, Summaries of *Papers Presented at the Annual Meeting of the Optical Society of America*, Nov. 3–8, 1991, San Jose, Calif., 1991 Technical Digest Series, vol. 17, Postconference Edition, Abstract MZ6, M. Bashkansky and J. Reintjes, p. 28.

*Holography and four-wave mixing to see through the skin*, Hendrik J. Gerritsen, SPIE vol. 519, Analog Optical Processing and Computing (1984), pp. 128–131.

*Time-gated imaging through scattering media using stimulated Raman amplification*, M. D. Duncan, R. Mahon, L. L. Tankersley, and J. Reintjes, 1991 Optical Letters, vol. 16, No. 23, Dec. 1, 1991; 1991 Optical Society of America, pp. 1868–1870.

*Chrono-Coherent Imaging for Medicine*, Kenneth G. Spears, Jenifer Serafin, Nils H. Abramson, Xinming Zhu, and Hans Bjelkhagen, IEEE Transactions on Biomedical Engineering, vol. 36, No. 12, Dec. 1989, pp. 1201–1221.

(List continued on next page.)

Primary Examiner—Lee S. Cohen
Assistant Examiner—Brian L. Casler
Attorney, Agent, or Firm—Thomas E. McDonnell; George Jameson

[57] ABSTRACT

A method and apparatus for imaging an object that is part of, embedded in or viewed through a scattering medium is provided. A first broadband beam generator, such as a broadband pulse laser, provides a first broadband beam. A second broadband beam generator, such as a Raman Stokes generator disposed to receive the first broadband beam, generates a second broadband beam capable of correlation with the first broadband beam. A coherent anti-Stokes Raman scattering material is disposed to receive the second broadband beam after dispersion in the scattering medium. A variable delay path also illuminates the coherent anti-Stokes Raman scattering material with the first broadband beam. The coherent anti-Stokes Raman scattering material produces an anti-Stokes beam which contains an extracted image of an object in the scattering medium, which image is recorded on a photodetector.

20 Claims, 3 Drawing Sheets

OTHER PUBLICATIONS

*Controlled picosecond gating and amplification of ultrafast optical signals,* G. L. Olson and G. E. Bush, Applied Physics Letters, vol. 27, No. 12, Dec. 15, 1975, pp. 684–686.

*Picosecond-gated optical amplifier,* G. E. Busch, K. S. Greve and G. L. Olson; R. P. Jones and P. M. Rentzepis, Applied Physics Letters, vol. 27, No. 8, Oct. 15, 1975, pp. 450–452.

*Time-resolved transilliumination for medical diagnostics,* S. Angersson-Engels, R. Berg, and S. Svanberg, O. Jarlman, Optics Letters, vol. 15, No. 21, Nov. 1, 1990, pp. 1179–1181.

*Electronic holography and speckle methods for imaging through tissue using femtosecond gated pulses,* E. Leith, H. Chen, Y. Chen, D. Dilworth, J. Lopez, R. Masri, J. Rudd and J. Valdmanis, Applied Optics, vol. 30, No. 29, Oct. 10, 1991, pp. 4204–4210.

*An Optical Up-Conversion Light Gate With Picosecond Resolution,* H. Mahr and Mitchell D. Hirsch, Optics Communications, vol. 13, No. 2, Feb. 1975, pp. 96–99.

APPARATUS FOR IMAGING AN OBJECT IN OR THROUGH A SCATTERING MEDIUM USING COHERENT ANTI-STOKES RAMAN SCATTERING

CROSS REFERENCE TO RELATED APPLICATION

This application is related to U.S. application Ser. No. 07/861,213 filed on Mar. 31, 1992 by Reintjes, Duncan, Mahon, Tankersly, Waynant and Bashkansky and entitled "Time-Gated Imaging Through Dense-Scattering Materials Using Stimulated Raman Amplification" which is herein incorporated by reference.

BACKGROUND OF THE INVENTION

1. Field of the Invention

The present invention relates to imaging devices and particularly to an apparatus and method for the time-gated optical examination of objects that are part of, embedded in or viewed through dense scattering materials using coherent anti-Stokes Raman scattering.

2. Description of the Related Art

Images of objects that are part of, embedded in, or viewed through a medium in which a significant amount of multiple path scattering occurs are usually blurred or otherwise degraded in resolution or completely obscured because the different paths over which the scattered radiation travels causes the image to appear to arise from more than one location within the scattering medium. FIG. 1 illustrates a scattering medium illuminated by a light beam 60. When the light beam 60 travels through the scattering medium 10, the light is scattered and emitted as beam 65. There are several methods that can be used to overcome this problem, with each having certain disadvantages.

A first method involves the spatial filtering of the image to include only those rays that are not deviated too far from the axis of the optical system. The limitations of this first method occur because the spatial frequencies of the scattered radiation can overlap those required to form the image of the object. Either the resolution with which the object can be imaged is limited, or the scattered radiation cannot be filtered out effectively.

A second method of overcoming the blurring of the image is to time gate the transmitted signal so that only the earliest light that emerges from the scattering medium is recorded by a detector. This "first light" either is not scattered, or is scattered over a relatively short path compared to light that emerges later, and therefore provides the least amount of image degradation. The degree of improvement provided by this second method depends on the length of the scattering path over which the detected signal is integrated, which, in turn, is determined directly by the duration of the time gate. In general, the shorter the time gate, the better the image, down to some characteristic time that is determined by the scattering characteristics of the medium. Imaging through dense scattering materials, such as biological tissue, or solids or liquids that appear translucent or even opaque to the unaided eye can require gating times of the order of 10 picoseconds or less.

There are several techniques currently used to perform such time-gated imaging measurements, including various forms of electronic gating and optical gating. Electronic gating can be accomplished either by gating a photoelectric image tube directly, or by switching some other part of the photoelectric detection circuit. These techniques are currently limited to gating times of the order of 50–100 picoseconds (psec) or longer, corresponding to minimum scattering paths of the order of 1.5–3 centimeters (cm) by the limitations of available electronic switching devices.

Another technique involves the use of picosecond or femtosecond pulses for illumination of the object, followed by an optical gating technique to provide the time resolution. Such techniques can provide time gates in the picosecond or subpicosecond regime, depending on the length of the optical pulse. For comparison with electronic gating methods, a time gate of 100 femtoseconds corresponds to a scattering path of 0.003 cm.

One gating technique suitable for picosecond or femtosecond pulses is holography, in which the image is detected only by a coincidence between the illumination pulse and a reference pulse of the desired length. Conventional holography, in which the image is recorded on high resolution photographic film, requires a substantial amount of light in the transmitted signal to interfere with the reference pulse to establish the holographic record. It thus limits the extinction in the sample that can be accommodated. Electronic holography, in which the fringes are detected with a sensitive two-dimensional camera and the hologram is reconstructed through computer analysis, overcomes the sensitivity problem, allowing greater attenuation in the sample. However, all of the transmitted light is recorded at the detector. If a large fraction of the transmitted light is contained in the non-image bearing tail that is delayed through scattering, the interference fringes that form the hologram will be washed out, and the noise in the image will be increased until the image is totally obscured.

Holography can also be accomplished with broadband, long-pulse laser light, in which the gate time is determined by the inverse of the bandwidth of the light. This approach provides subpicosecond gate times without the need for subpicosecond technology. However, as it has been applied to date, it suffers from the same disadvantages described above for picosecond holography: large signal requirements and relatively low contrast between the image-bearing portion of the transmitted light and the non-image-bearing tail.

Another technique for short pulse gating is the use of a Kerr shutter, in which the transmission of light through a cell between crossed polarizers is controlled by a second pulse of light. The gate times for this approach can be of the order of picoseconds, depending on the duration of the controlling light pulse and the response time of the active medium in the Kerr gate. This technique suffers from limitations in contrast because of leakage of the wrong polarization through the polarizers, and losses in the Kerr gate because the transmission is less than 100%. Contrast can be increased by cascading gates, but only at the expense of overall transmission. The loss of transmission can be especially detrimental for viewing through highly attenuating samples in which there is a limit on allowable irradiation levels, such as for living tissue.

Image amplification with picosecond time-gated amplifiers have also been described in the prior art. These amplifiers have been based on dye amplifiers pumped by picosecond laser pulses. By themselves the dye amplifiers have relaxation times of the order of several nanoseconds and, therefore, gating times of the same order of magnitude. Picosecond gating times were achieved by raising the dye concentration and pumping level to such a degree that substantial radiation from the upper laser level occurs, leading to population "dumping" and reduced lifetime of the upper state. The limitations of these amplifiers are that the high level of fluorescence necessary to produce the short gating time contributes a background on top of the amplified image, limiting the sensitivity and increasing the noise level. The amplifiers have had gains of only 100 to 1000, limiting the degree of contrast with the delayed light. Finally, fundamental considerations of the noise level of amplifiers show that the minimum noise level occurs when the time-bandwidth product $\Delta\nu\Delta t = 1$. The dye fluorescence is radiated over the full bandwidth of the dye amplifier, of the order of 500 cm$^{-1}$. As a result, for gating times of the order of 10 picoseconds, the time-bandwidth product is in excess of 100, increasing the minimum noise value by the same factor.

Several other techniques are also possible. Streak cameras can be used to record the image. Time resolutions down to 2 picoseconds are currently possible. However, only a one-dimensional image is obtained, requiring scanning to produce a two-dimensional image. In addition, the streak cameras are of limited sensitivity, limiting their utility in detecting low-level signals. Another approach that uses time-gating involves the technique of four-wave mixing. In this approach the signal beam impinges on a non-linear medium that is being irradiated with co-propagating picosecond light pulses. Conversion of the signal light takes place only while the gating pulse is present. The main drawback to this approach is the combination of low conversion efficiencies associated with the conversion process (10% or less), coupled with limitations on the allowable illumination signal as set by the ANSI standards for irradiation of living tissue. Four-wave mixing using phase conjugation has also been suggested. The disadvantage of this technique is that, while phase conjugation can correct refractive distortion, it does not correct for scattering distortion due to fundamental considerations.

Non time-gating techniques also include the use of holographic recordings using spatial correlation to discriminate against the non image-bearing light. This approach has the same limitations due to low contrast with non-correlated light as discussed above for holography. Finally, use may be made of absorption in the sample to attenuate the longer paths associated with the multiple scattered light. This can work in materials that are highly absorbing, but not for materials that are primarily scattering rather than absorbing.

A recently developed system involves time gating by stimulated Raman amplification using short light pulses.

SUMMARY OF THE INVENTION

It therefore is an object of the present invention to provide an apparatus and method for imaging an object that is embedded in or viewed through a scattering medium using either long or short duration pulses.

Another object of the present invention to provide a method and apparatus for imaging an object that is embedded in or viewed through a scattering medium which provides both short time resolution and long duration pulse light illumination to the scattering medium.

Another object of the present invention to provide a method and apparatus for imaging an object that is embedded in or viewed through a scattering medium capable of effectively removing background illumination caused by scattering within the scattering medium and still provide an extracted image of sufficient intensity and quality.

A further object of the present invention is to provide a method and apparatus for optically extracting an image of an object in a beam of light emitted from a scattering medium.

In order to achieve the foregoing objects, in accordance with the purposes of the present invention as described herein, a method and apparatus for imaging an object that is embedded in or viewed through a scattering medium is provided. A first broadband beam generator, such as a broadband pulsed laser, provides a first broadband beam. A second broadband beam generator, such as a Raman Stokes generator disposed to receive the first broadband beam, generates a second broadband beam capable of amplitude correlation with the first broadband beam. A coherent anti-Stokes Raman scattering material (CARS) is disposed to receive the second broadband beam after dispersion in the scattering medium. A variable delay path also illuminates the coherent anti-Stokes Raman scattering material with the first broadband beam. The coherent anti-Stokes Raman scattering material produces an anti-Stokes beam which contains an image of an object in the scattering medium. The broadband beam can be in the form of either a short duration pulse or a broadband stochastic pulse.

The above-mentioned and other objects of the present invention will become more apparent from the following description when read in conjunction with the accompanying drawings. However, the drawings and descriptions are merely illustrative in nature and not restrictive.

DESCRIPTION OF THE PREFERRED EMBODIMENTS

Figure 1:
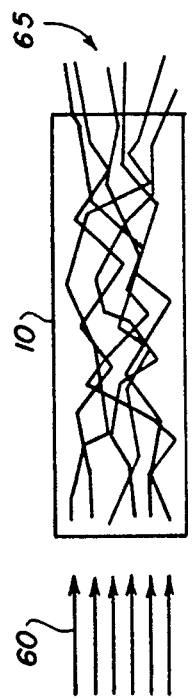
FIG. 1 illustrates a diagram of a scattering medium.
Figure 2:
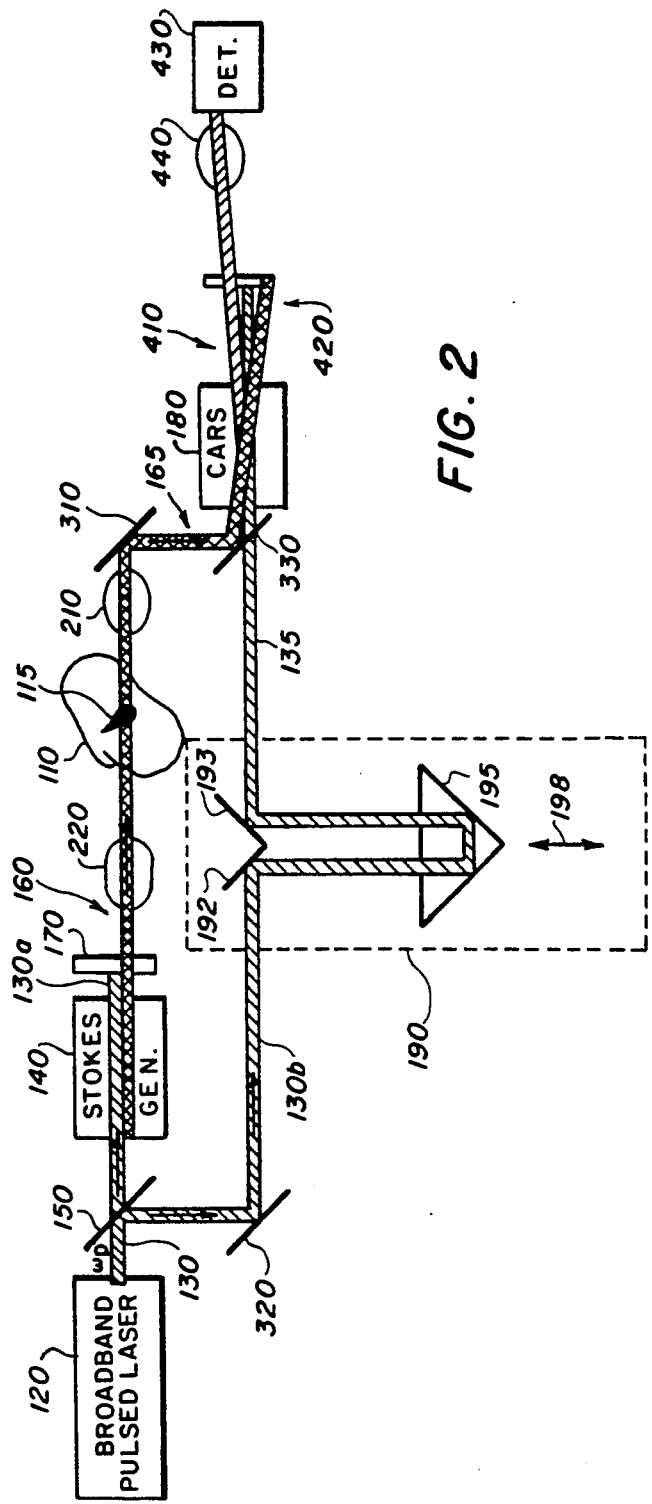
FIG. 2 illustrates a schematic block diagram of the method and apparatus for imaging an object embedded in or viewed through a scattering medium according to a preferred embodiment of the present invention.

FIG. 2 illustrates a method and apparatus according to a preferred embodiment of the present invention for imaging an object embedded in or viewed through a scattering medium 110. A broadband pulse laser 120 provides a broadband beam 130. The broadband pulse laser 120 can provide either a pulse of short duration or a pulse of broadband stochastic light with a relatively long duration. Imaging of objects embedded in or viewed through the scattering medium 110 can be accomplished with short time resolution with either pulse format within the scope of the present invention. However, for purposes of this description of the invention, the pulse laser 120 will be discussed as providing a broadband stochastic pulse of relatively long duration. Specific values of the pulse duration and resolution time are determined by the characteristics of the scattering material 110. For biological tissue, for example, a pulse duration of the order of 1 nanosecond ($10^{-9}$ seconds) is preferred, with a time resolution of the order of, for example, 1-10 picoseconds ($10^{-12}$ seconds) being preferred.

A relatively small portion 130a of the broadband stochastic beam 130 output of the broadband pulse laser 120 is passed through a beam splitter 150 to illuminate a Stokes generator 140, and the remaining larger portion 130b is reflected by the beam spitter 150. A Stokes generator 140 generates a second broadband stochastic beam 160 having amplitude correlation with the first broadband stochastic beam 130. A filter 170 passes the second broadband stochastic beam 160 and blocks the first broadband stochastic beam 130a at an output of the Stokes generator 140. Alternatively, the Stokes generator 140 can be replaced by a second laser for generation of the second broadband stochastic beam as long as the second broadband stochastic beam has amplitude correlation with the first broadband stochastic beam generated by the broadband laser 120.

The second broadband stochastic beam 160 scatters within the scattering medium 110 to produce a scattered second broadband stochastic beam 165 which is then projected upon a coherent anti-Stokes Raman scattering (CARS) material 180. The portion 130b of the first broadband stochastic beam 130 that is reflected by the beam splitter 150 is passed through an adjustable reference path 190 to produce a delayed first broadband stochastic beam 135, which is also directed into the coherent anti-Stokes Raman scattering material 180.

The second broadband stochastic beam 165 provided from the scattering medium 110 to the coherent anti-Stokes Raman scattering material 180 can be directed at an angle or parallel with respect to the first broadband stochastic beam provided from the adjustable reference path 190 to the coherent anti-Stokes Raman scattering material 180, depending on the phase-matching requirements of the particular CARS material 180 that is used. Furthermore, the second broadband stochastic beam 165 and the first broadband stochastic beam 135 must illuminate a common portion of the coherent anti-Stokes Raman scattering material 180. The larger the common portion of the CARS material 180 that is illuminated by the beams 135 and 165, the more intense will be the anti-Stokes beam 410 (to be discussed) from the CARS material 180 and the greater the resolution of the final image. It is preferable that the object 115, which is shown embedded in the scattering material 110 in FIG. 2, be imaged into the CARS material 180 by a lens or optical train 210, located between the scattering medium 110 and the CARS material 180. An optical train 220, such as a telescope or lens combination, can be provided between the filter 170 and the scattering medium 110 to adjust the beam width of the second broadband stochastic beam 160 provided to the scattering medium 110. Further, as can be appreciated, various mirrors 310 and 320 and a beam splitter 330 are preferable for directing the beams. For example, the mirror 310 could be positioned to reflect the beam 165 from the optical train 210 off of the beam splitter 330 into the CARS material 180. In a like manner, the mirror 320 could be positioned to reflect the beam 130b from the beam splitter 150 into the adjustable reference path 190.

The beam splitter 330 enables superposition of the first broadband stochastic beam 135 and the second broadband stochastic beam 165 on the coherent anti-Stokes Raman scattering material 180. The order of the mirrors 310 and 320, the beam splitter 330 and lenses such as the optical train 210 is not important.

An anti-Stokes beam 410 is produced within the coherent anti-Stokes Raman scattering material 180. The first broadband stochastic beam 135 and the second broadband stochastic beam 165 travel straight through the CARS material, as shown in FIG. 2. The anti-Stokes beam 410 is created at an angle with respect to the other beams 135 and 165, as determined by the appropriate phase-matching properties of the CARS material 180. The anti-Stokes beam 410 contains image information about an object 115 that is part of, embedded in, or viewed through the scattering material 110 without defects due to scattering in the scattering medium 110. The defects in the beam 165 are removed within the coherent anti-Stokes Raman scattering material 180 when combined with a properly timed reference beam provided by the first broadband stochastic beam 135, as will be later discussed below.

A filter 420 is preferably used to pass the anti-Stokes beam 410 and block both the first broadband stochastic beam 135 and the second broadband stochastic beam 165. The filter 420 can be sensitive to frequency or alternatively can be a polarization filter to remove the first broadband stochastic beam 135 and the second broadband stochastic beam 165 and pass the anti-Stokes beam 410 therethrough, through an optical element 440, such as a lens or a compound lens, to form an image of the object 115 on a conventional detector 430, such as a charge coupled device (CCD) array, a two-dimensional photo detector or a scanning one-dimensional photo detector array, which receives the anti-Stokes beam 410 to detect an image of the object 115 or the like in the scattering medium 110. Thus, it is possible to use a light beam to view an object within a scattering medium even though the light beam is scattered within the scattering medium to obstruct optical viewing of the object by the naked eye or other conventionally known imaging technique.

The anti-Stokes beam will emerge from the CARS material 180 at an angle relative to the beams 135 and 165, depending upon the angles at which the beams 135 and 165 are directed into the coherent anti-Stokes Raman scattering material 180. Thus, it is also possible that a filter can be avoided altogether and the detector 430 placed at an angle sufficient to receive the anti-Stokes beam 41 and not receive the other two beams 135 and 165, as discussed below with respect to FIG. 3. Further conventional optics, such as the illustrated lens 440, can also be utilized between the filter 420 and the detector 43 to adjust the size of the anti-Stokes beam 410 to the size of the detector 430.

The coherent anti-Stokes Raman scattering material 180 can be any liquid, solid, gas or plasma material exhibiting a Raman shift. When the material 180 is a gas, it can be held in a conventional cell having transparent windows that do not affect the beams. The coherent anti-Stokes Raman scattering material 180 can be an atomic vapor such as, for example, sodium, mercury or selenium. Further, the coherent anti-Stokes Raman scattering material can be a molecular gas such as hydrogen, or an organic liquid such as alcohol. Combinations of these materials may be possible for the coherent anti-Stokes Raman scattering material 180. Additionally, combinations of these materials with other materials, such as inert gases, may be possible for phase matching. The coherent anti-Stokes Raman scattering material 180 should also have a linewidth much less than the bandwidth of the broadband laser 120.

For example, imaging of objects embedded in biological tissue requires resolution times of the order of 1 picosecond or less. The resolution time is the inverse of the bandwidth of laser 120. Hydrogen gas at a pressure of 150-200 psi (10-13.6 atmospheres) has a response time (inverse of linewidth) of the order of 0.5 nsec, which satisfies the requirement of being greater than the correlation time of the laser light.

The Stokes generator 140 should preferably use the same material as the coherent anti-Stokes Raman scattering material 180. If the material is a gas, the gas pressure sould be the same in both the Stokes generator 140 and the CARS cell 180.

The type of broadband pulse laser 120 is not important so long as it is capable of delivering pulses of broadband light. For example, the broadband pulse laser 120 can be a dye laser, an excimer laser or a solid state laser. The solid state laser can be made of, e.g., titanium sapphire, alexandrite, Li:CAF or Li:SAF. The broadband pulse laser 120, in an example for viewing biological tissue with an exemplary coherent anti-Stokes Raman scattering material 180 of hydrogen, can have a center frequency of 565 nanometers (nm) with a total bandwidth of 10 nanometers. For viewing through biological tissue, for example, the broadband pulse laser 120 preferably produces long pulses of at least about one nanosecond ($10^{-9}$ second). A long pulse is preferred for viewing tissue to avoid exceeding illumination levels recommended by the American National Standards Institute (ANSI).

The broadband pulse laser 120 generates the first broadband stochastic beam with a pump frequency of preferably $\omega_p$. The coherent anti-Stokes Raman scattering material 180 provides the anti-Stokes beam 410 without the defects produced from scattering within the scattering medium 110 when the frequency of the beams is provided as follows. The Stokes generator 140 generates the second broadband stochastic beam 160 with a frequency $\omega_s$ dependent on the type of material of the Stokes generator 140. The Stokes generator 140 preferably is the same material as the material of the coherent anti-Stokes Raman scattering material 180 to produce like magnitude frequency shifts $\omega_o$. The Stokes generator 140 causes a frequency shift $\omega_o$ of a pump frequency $\omega_p$ of the broadband stochastic beam 130. Thus, the second broadband stochastic beam has a frequency of $\omega_s = \omega_p - \omega_o$. The coherent anti-Stokes Raman scattering material 180 has been found to exhibit characteristics that produce the anti-Stokes beam 410 with a frequency $\omega_{as} = \omega_p + \omega_0$.

The excitations of the molecules that accompany the production of the frequencies discussed above causes performance of a correlation function on the beams 135 and 165 during the production of the anti-Stokes beam 410. The correlation function performed in the coherent anti-Stokes Raman scattering material 180 produces the anti-Stokes beam 410 with an energy equal to an integral of the laser amplitude $A_{Lref}$ correlated with the Stokes beam amplitude $A_S$ with respect to time according to the following equation:

$$E_{As} \propto |\int A_{Lref}(t') \cdot A_S^*(t') dt'|^2.$$

This is a correlation function of beam 165 when:

$$A_S^*(t') \propto A^*_{Lref}(t' - \tau).$$

Besides the frequencies of the beams, the timing of the pump being provided by the first broadband stochastic beam 13 depends upon the characteristics, such as the length of the scattering medium 110, to produce the anti-Stokes beam 410 in the coherent anti-Stokes Raman scattering material 180 so that the anti-Stokes beam 410 represents an object 115 in the scattering medium 110 without distortions therein. The timing of the first broadband stochastic beam 135 with respect to the second broadband stochastic beam 165 is adjusted by the adjustable reference path 190. The pathlength of the adjustable reference path 190 is adjusted to vary the arrival of the pulses in the beams 135 and 165 on the coherent anti-Stokes Raman scattering material 180. The relative timing between the beams 135 and 165 should be chosen so that the reference beam 135 is correlated in time in the coherent anti-Stokes Raman scattering material 180 with that part of the beam 165 that is not significantly scattered by the medium 110.

The adjustable reference path 190 preferably contains conventional mirrors 192 and 193 and a retroreflector 195 such as a corner cube or rooftop prism. The retroreflector 195 is translatable in the directions of double-arrows 198. Translation of the retroreflector 195 can adjust the path length and thus the timing of the first broadband stochastic beam 130a. Typically, the rooftop prism, for example, is mounted on a translatable stage (not shown) moved by, for example, a screw or electric motor (not shown) to thus shorten or lengthen the optical path through the adjustable reference path 190.

Figure 3:
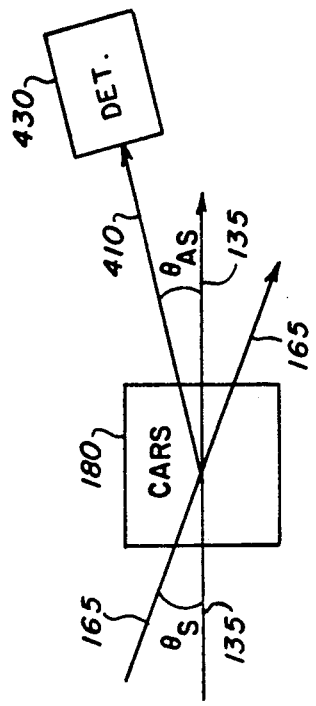
FIG. 3 illustrates a schematic block diagram of a method and apparatus for imaging an object embedded in or viewed through a scattering medium according to a modification of the embodiment of FIG. 2.

FIG. 3 illustrates a modification of the embodiment of FIG. 2. In FIG. 3, the detector 430 is provided at an angle sufficient to receive the anti-Stokes beam 410 but not receive the first broadband stochastic beam 135 and the second broadband stochastic beam 165. It is noted that the angle $\Theta_s$ between the beams 135 and 136 and the angle $\Theta_{as}$ of the anti-Stokes beam 410 are fixed by nature for a particular wavelength of light and material of the coherent anti-Stokes Raman scattering cell 180. It is possible for $\Theta_s$ to be zero and therefore both of the beams 165 and 135 to be parallel. However, it has been found that, for a particular wavelength of light, $\Theta_s$ can be about 5 milli-radians (mr) for a vibrational shift and about 400 micro-radians ($\mu r$) for a rotational shift if hydrogen is used for the coherent anti-Stokes Raman scattering material 180.

Figure 4A:
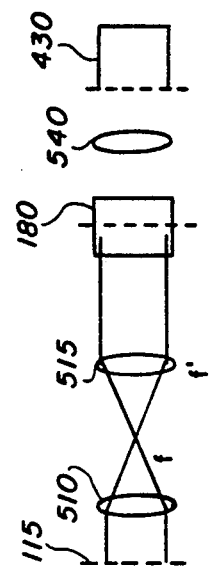
FIGS. 4(a) and 4(b) show in detail a portion of the embodiment of FIG. 2, illustrating an exemplary implementation for forming an image in the CARS cell of the object under study and transferring that image to the optical detector.
Figure 4B:
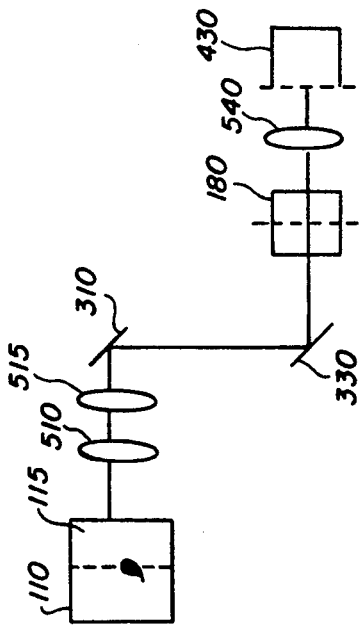

FIGS. 4(a) and 4(b) and FIGS. 5(a) and 5(b) illustrate optics for transporting the image of the object 115 to the CARS cell or material 180 and to the optical detector 430. FIG. 4(a) illustrates an image relay system comprised of lenses 510 and 515 between the scattering medium 110 and the coherent anti-Stokes Raman scattering material 180. Lens 540 is illustrated between the coherent anti-Stokes Raman scattering material 180 and the detector 430. Lenses 510 and 515 relay the image of the object 115 to the CARS cell or material 180. Lens 540 forms an image of the object 115 on the detector 430. FIG. 4(b) shows the ray paths involved in imaging.

Figure 5B:
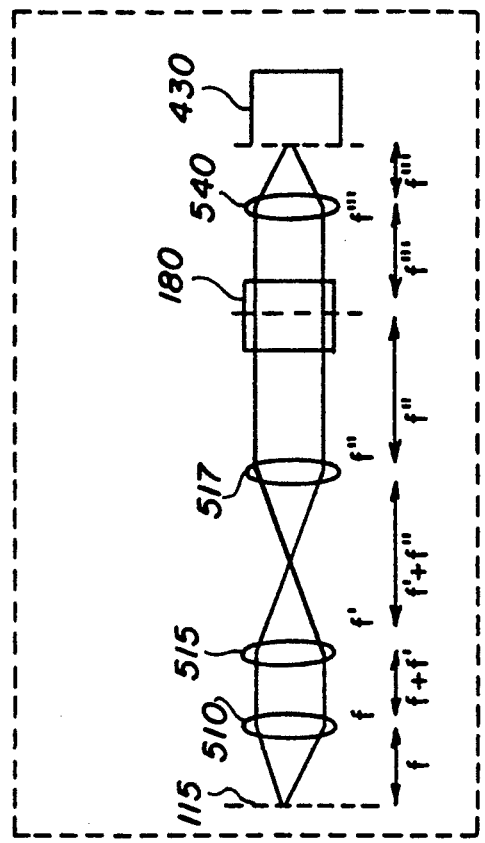
FIGS. 5(a) and 5(b) show a modification of the implementation of FIGS. 4(a) and 4(b) that can reduce noise in the detected image.
Figure 5A:
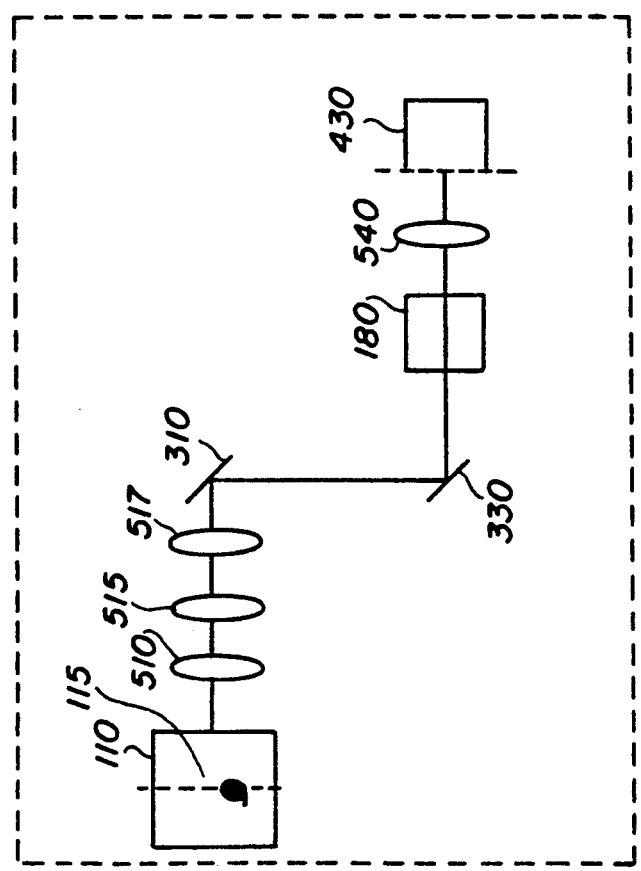

FIG. 5(a) and 5(b) illustrate a preferred form of photon noise reduction by using a Fourier transform within the coherent anti-Stokes Raman scattering material 180. Lenses 510, 515 and 517 are provided together with lens 540. Lenses 510, 515 and 517 are provided between the scattering medium 110 and the coherent anti-Stokes Raman scattering material 180 and the lens 540 is provided between the coherent anti-Stokes Raman scattered material 180 and the detector 430. The lens 510 forms a Fourier transform of the object 115, which is relayed to the CARS cell 180 by the lenses 515 and 517. Lens 540 performs an additional Fourier transform, reconstructing the image of the object 115 at the detector 430. FIG. 5(b) further illustrates the ray paths involved in the Fourier imaging.

While the invention has been illustrated and described in detail in the drawings and foregoing descriptions, it will be recognized that any changes and modifications will occur to those skilled in the art. It is therefore intended by the appended claims, to cover such changes and modifications as fall within the true spirit and scope of the invention.

What is claimed and desired to be secured by Letters Patent of the United States is:

1. An apparatus for imaging an object that is part of, embedded in or viewed through a scattering medium, said apparatus comprising:
   a first broadband beam generator providing a first broadband beam;
   a second broadband beam generator generating a second broadband beam capable of amplitude correlation with the first broadband beam; and
   a coherent anti-Stokes Raman scattering material responsive to the first broadband beam and to the second broadband beam after dispersion in the scattering medium for producing a beam containing image information of the object in the scattering material.

2. The apparatus of claim 1 wherein:
   said first broadband beam generator is a long pulse broadband laser.

3. The apparatus of claim 1 wherein:
   said first broadband beam generator provides a first broadband stochastic beam.

4. The apparatus of claim 1 further including:
   an adjustable optical path length optically disposed between said first broadband beam generator and said coherent anti-Stokes Raman scattering material.

5. The apparatus of claim 1 wherein:
   said second broadband beam generator comprises a Stokes generator optically disposed along an optical path between said first broadband beam generator and the scattering medium to provide the second broadband beam to the scattering medium in correlation with the first broadband beam.

6. The apparatus of claim 5 further including:
   a filter optically disposed between said Stokes generator and the scattering medium, said filter having characteristics sufficient to pass the second broadband beam and block the first broadband beam.

7. The apparatus of claim 5 wherein:
   said coherent anti-Stokes Raman scattering material comprises a material exhibiting a Raman shift; and
   said Stokes generator comprises said same material exhibiting the Raman shift.

8. The apparatus of claim 1 further including:
   a filter optically disposed at an output of the coherent anti-Stokes Raman-scattering material, said filter having characteristics sufficient to block both the first and second broadband beams and to pass an anti-Stokes beam generated in said coherent anti-Stokes Raman scattering material.

9. The apparatus of claim 8 further comprising:
   a detector optically disposed in line with said filter to record an image in the anti-Stokes beam.

10. The apparatus of claim 1 wherein:
    said first and second broadband beam generators provide first and second broadband stochastic beams, respectively;
    said coherent anti-Stokes Raman scattering material produces an anti-Stokes beam at an angle different than that of each of said first and second broadband stochastic beams; and
    said apparatus further includes a detector optically disposed along the angle to detect the anti-Stokes beam and avoid the first and second broadband stochastic beams.

11. The apparatus of claim 1 wherein:
    said coherent anti-Stokes Raman scattering material comprises a material exhibiting a Raman shift.

12. The apparatus of claim 11 wherein:
    said material exhibiting a Raman shift is selected from a group of atomic vapors consisting of sodium, mercury and selenium.

13. The apparatus of claim 11 wherein:
    said material exhibiting a Raman shift comprises a hydrogen gas.

14. The apparatus of claim 11 wherein:
    said material exhibiting a Raman shift comprises an organic liquid including alcohol.

15. The apparatus of claim 11 wherein:
    said material exhibiting a Raman shift is a material having a line width characteristic narrower than a line width characteristic of the first broadband beam generated by said first broadband beam generator.

16. The apparatus of claim 1 wherein:
    said coherent anti-Stokes Raman scattering material has a density sufficient to cause a high gain.

17. The apparatus of claim 1 further including:
    a pair of Fourier transform lenses optically disposed between the scattering medium and said coherent anti-Stokes Raman scattering material.

18. The apparatus of claim 17 further including:
    another pair of Fourier lenses optically disposed on opposite sides of said coherent anti-Stokes Raman scattering material with focal points thereof within said coherent anti-Stokes Raman scattering material.

19. An apparatus for imaging an object that is part of, embedded in or viewed through a scattering medium, said apparatus comprising:
    beam generating means for generating a first broadband stochastic beam and a second broadband stochastic beam in correlation with the first broadband stochastic beam; and
    Raman scattering means for performing coherent anti-Stokes Raman scattering in response to the second broadband stochastic beam after dispersion in the scattering medium and in response to the first broadband stochastic beam.

20. A method for imaging an object that is part of, embedded in or viewed through a scattering medium, said method comprising the steps of:
    generating a first broadband stochastic beam;
    generating a second broadband stochastic beam correlated with the first broadband stochastic beam; and
    performing a coherent anti-Stokes Raman scattering on the second broadband stochastic beam after dispersion in the scattering medium and on the first broadband stochastic beam.

* * * * *